US00PP22140P2

(12) United States Plant Patent
Dozier, Jr. et al.

(10) Patent No.: US PP22,140 P2
(45) Date of Patent: Sep. 13, 2011

(54) KIWI PLANT NAMED 'AU GOLDEN TIGER'

(50) Latin Name: ***Actinidia chinensis* Planch.**
Varietal Denomination: Au Golden Tiger

(75) Inventors: William Alfred Dozier, Jr., Opelika, AL (US); Bryan Shelton Wilkins, LaFayette, AL (US); Jim Pitts, Clanton, AL (US); Curtis Jay Hansen, Opelika, AL (US); James D. Spiers, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/711,204

(22) Filed: Feb. 23, 2010

(51) Int. Cl.
*A01H 5/00* (2006.01)

(52) U.S. Cl. ..... Plt./156

(58) Field of Classification Search ..... Plt./156
See application file for complete search history.

(56) References Cited

PUBLICATIONS

Wall et al., "Vegetative and Floral Chilling Requirement of Four New Kiwi Cultivars of *Actinidia chinensis* and *A. deliciosa,*" (Hort Science 43(3):644-647, Jun. 2008.

Wall et al., "Determining a Maturity Index and the Effect of Chilling Requirements, and Cytokinin Applications on Three New Kiwi Cultivars," Thesis—Degree of Master of Science, Auburn University, Aug. 2006, 87 pages.

*Primary Examiner* — Susan McCormick Ewoldt

(74) *Attorney, Agent, or Firm* — Andrus, Sceales, Starke & Sawall, LLP

(57) ABSTRACT

A new and distinct cultivar of the species *Actinidia chinesis* Planch is described. This cultivar named 'AU Golden Tiger' was developed from seeds collected from an open pollinated 'AU Golden Dragon' fruit. The seedling has been reproduced by rooted cuttings and grafting and tested in replicated cultivar trials. It maintains all of its unique characteristics after each propagation. Its bloom period overlaps the bloom period of 'AU Golden Sunshine' and is the pollinizer for 'AU Golden Sunshine'.

3 Drawing Sheets

Latin name of the genus and species of the plant claimed: *Actinidia chinensis* Planch.

Variety denomination: 'AU GOLDEN TIGER'.

RELATED APPLICATIONS

U.S. patent application Ser. No. 12/711,219, filed on Feb. 23, 2010, and entitled "KIWI PLANT NAMED 'AU GOLDEN DRAGON'" and U.S. patent application Ser. No. 12/711,194, filed on Feb. 23, 2010, and entitled "KIWI PLANT NAMED 'AU GOLDEN SUNSHINE'" are both incorporated by reference herein. 'AU Golden Dragon' is the maternal parent of 'AU Golden Tiger'. 'AU Golden Tiger' blooms with and is the pollenizer for 'AU Golden Sunshine'.

BACKGROUND OF THE INVENTION

The new kiwi cultivar 'AU Golden Tiger' was developed from seed collected from open pollinated fruit of 'AU Golden Dragon' in 1998. The seed were planted and germinated in flats in a greenhouse in Alabama. Four weeks after germination the plants were potted in 4 inch pots and grown in the greenhouse. The following spring the greenhouse grown seedlings were potted into 1 gallon pots and grown through the year on a irrigated growing pad. In the spring of 2000 the plants were planted in the field and grown on a T-bar Trellis system and evaluated for growth and performance. 'AU Golden Tiger' was selected from this set of seedlings as a male pollenizer for 'AU Golden Sunshine' because it is the only male kiwi plant tested in Alabama that blooms with and overlaps the bloom period of 'AU Golden Sunshine'.

SUMMARY OF THE INVENTION

Seedlings developed from seeds collected from open pollinated 'AU Golden Dragon' fruit were grown and evaluated for potential new cultivars. 'AU Golden Tiger' has bloomed each year with 'AU Golden Sunshine'. The male parent of the 'AU Golden Tiger' seedling is unknown as the 'AU Golden Dragon' fruit from which the seeds were obtained were open pollinated.

The present invention relates to a new and distinct male kiwi cultivar of *Actinidia chinensis* Planch. The female parent is 'AU Golden Dragon' and the male parent is unknown. The new cultivar is able to be asexually reproduced as rooted softwood and hardwood cuttings or by grafting onto a seedling or rooted cutting grown rootstock. The unique characteristics come true to form and are established and transmitted through succeeding asexual propagations in central Alabama. In the climate of Alabama, vegetative bud break occurs during the last 10 days of March, and the bloom period occurs during the last week of April and first week of May depending on the climate during the season.

'AU Golden Tiger' produces flower buds in the first 5-7 nodes on a new shoot developing from the previous year's growth. There is usually one stalk per node with 3 to 5 flower buds on the stalk. It does not produce as many flowers per node as some of the other male cultivars such as 'Matua' (not patented) and 'Hortkiwi Meteor' (not patented). However, it is the only male kiwi plant which blooms with and overlaps the 'AU Golden Sunshine' bloom period.

DETAILED BOTANICAL DESCRIPTION

Kiwi plants are large deciduous shrubs that originated in China and are dioecious, can climb up to 25 feet, and have alternate, broadly rounded petiolate leaves. The cream colored flowers that grow in axillary cymes mature into ovate to oblong fruits (berries) with brownish, hairy skins. There are over 50 species in the genus *Actinidia*. The two *Actinidia* species of the most commercial importance are *deliciosa* and *chinensis*. 'Hort 16A' (patented) (U.S. Pat. No. 11,066) is the most important yellow flesh *chinensis* cultivar in the commercial trade. The kiwi plant is dioecious thereby requiring male pollinizers in the presence of the female plants to ensure fruit production. The male and female plants bloom period have to be at the same time for pollination to occur. The bloom period varies with each cultivar depending upon the chilling requirement and the growing degree hour requirement after the chilling requirement has been met. *Actinidia* are temperate zone plants that prefer well drained moist and rich soil and grows as well in a sunny as in a half-shady position.

The new cultivar 'AU Golden Tiger' is a male with imperfect flowers. It has an average of 167 stamens (range 160-173) per flower and vestigial pistils. Characteristics of the new cultivar in which it differs from the standard male kiwi cultivar 'Matua' (not patented) includes earlier blooming, a bloom period that overlaps the bloom period of 'AU Golden Sunshine', and bright orange flower petals. When the flower opens, the petal is creamy white (RHS 158C) but changes to a bright orange (RHS 169A) by the day after the bloom opens. Petal fall occurs 7-8 days after the flower opens.

Figure 1:
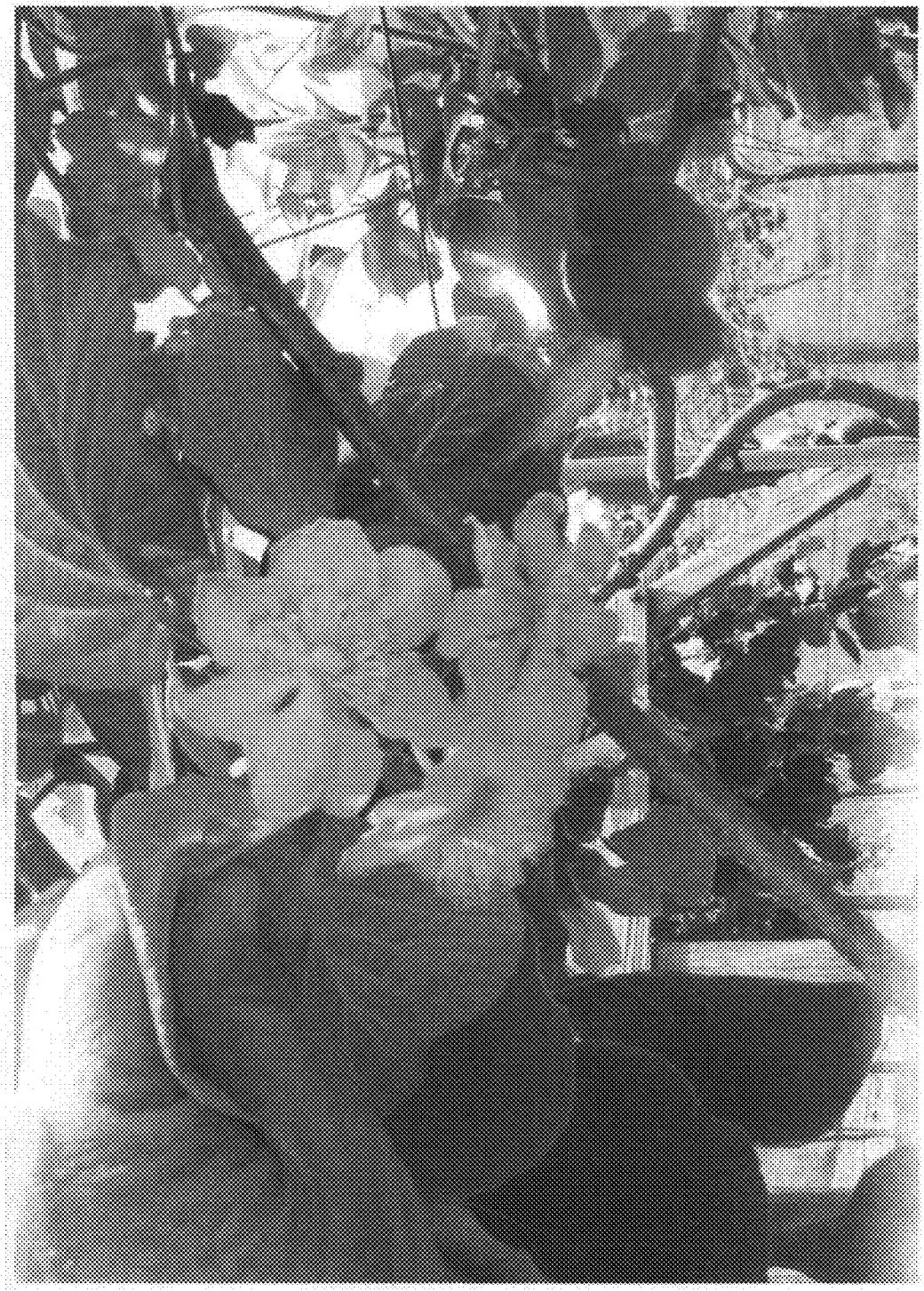
FIG. 1 is a photograph of 'AU Golden Tiger' flower on an 8 year old plant.
Figure 2:
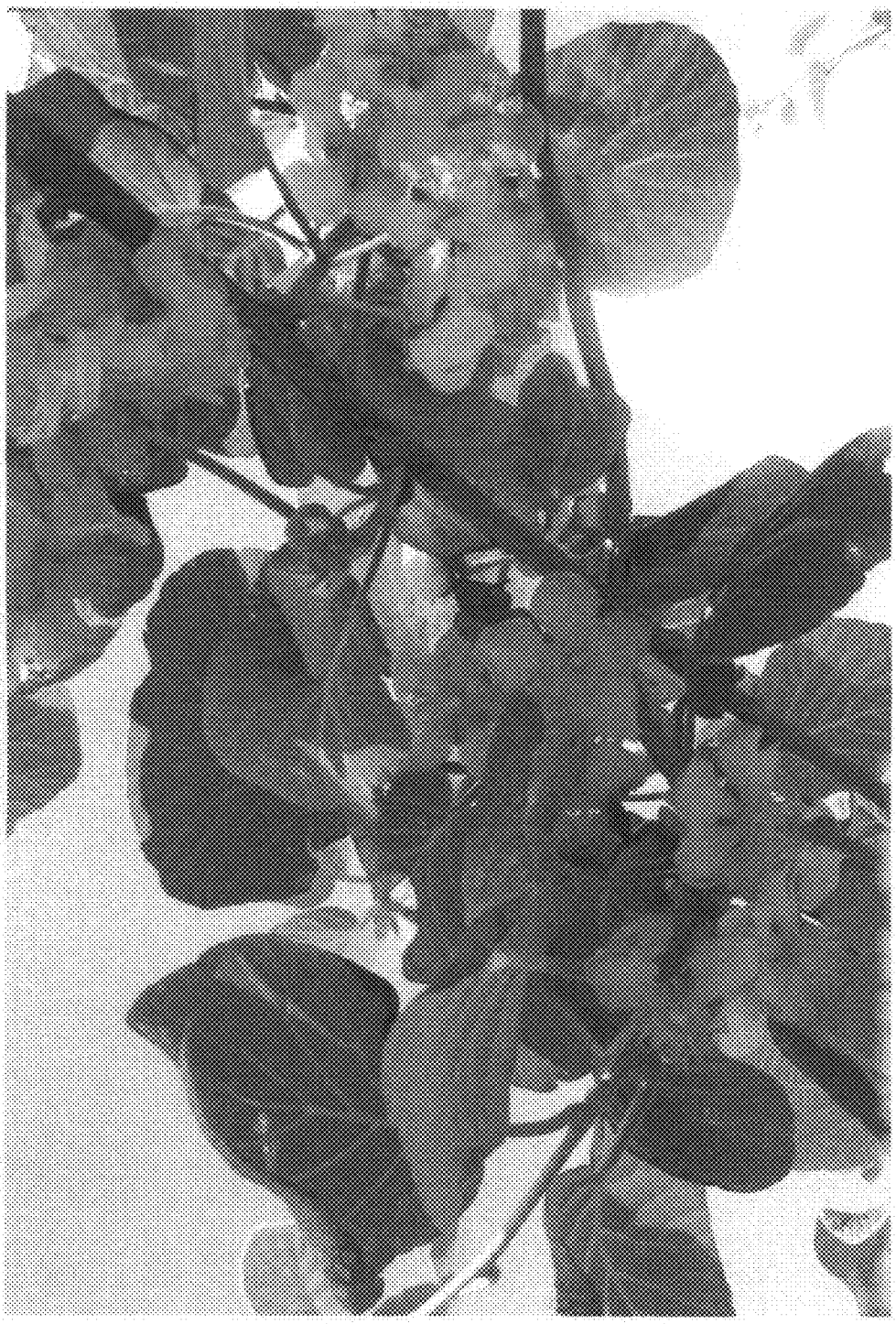
FIG. 2 is a photograph of 'AU Golden Tiger' bloom density on an 8 year old plant.
Figure 3:
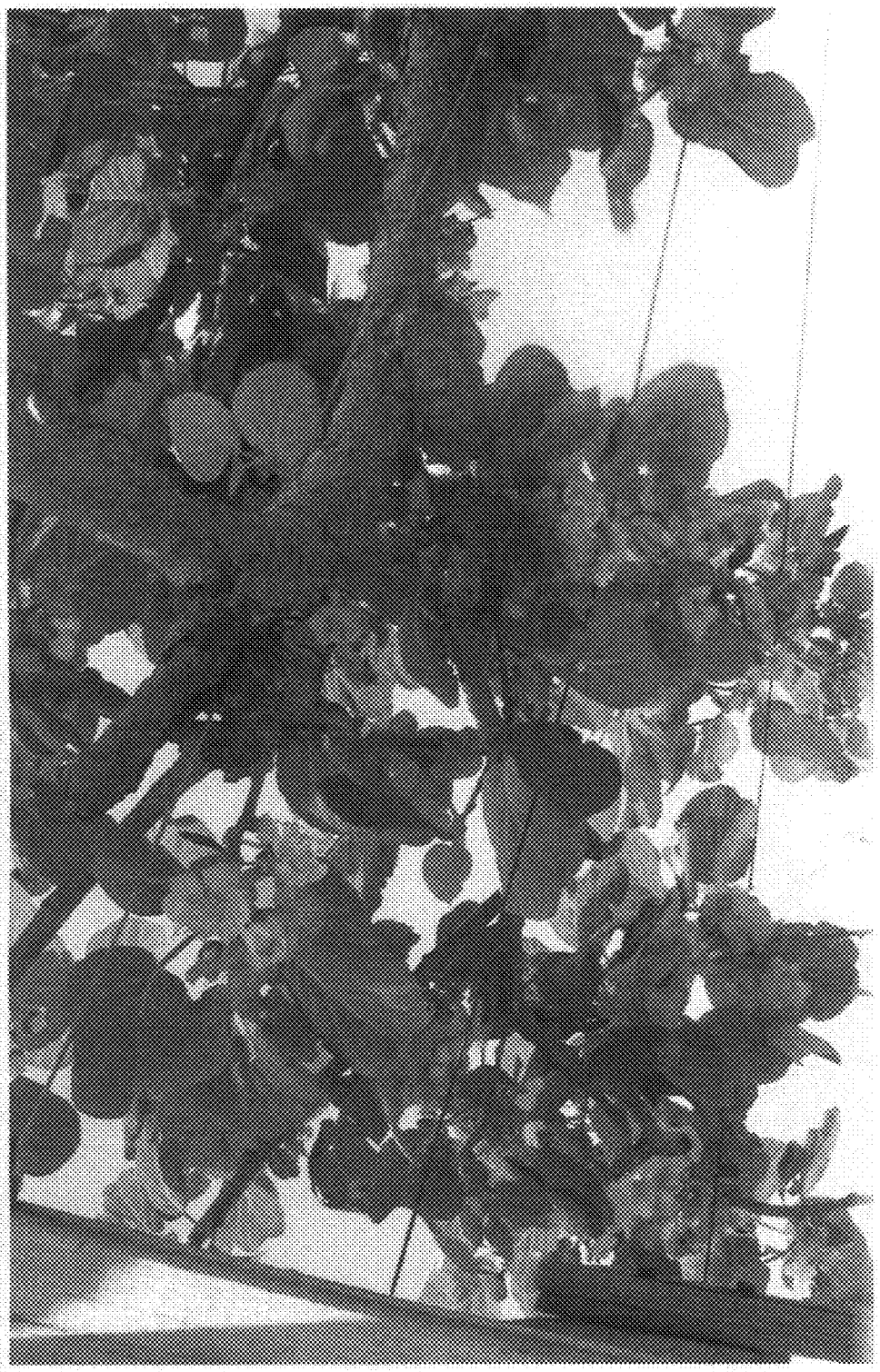
FIG. 3 is a photograph of 'AU Golden Tiger' full bloom stage showing white newly open flower with other changing to orange by second day after opening on an 8 year old plant.

'AU Golden Tiger' is able to be asexually reproduced as softwood and hardwood cuttings or by grafting onto a seedling or cutting grown rootstock with the unique characteristics being transferred through succeeding asexual propagations. 'AU Golden Tiger' has been propagated by rooting softwood and hardwood cuttings and by cleft grafting in Alabama. The distinctive characteristics of this new kiwi cultivar described in detail below have been observed in field experiments in central Alabama, US. The plants described in and shown in FIG. 3 were 8 years old. The 'Matua' cultivar was evaluated in the same field experiments and was used as the standard cultivar for comparison.

'AU Golden Tiger' is the male pollenizer used for pollination of 'AU Golden Sunshine'. 'AU Golden Dragon' is the maternal parent of 'AU Golden Tiger'. 'AU Golden Dragon' fruit matures 20 days before the fruit of 'AU Golden Sunshine' and 50 days before the fruit of 'Hort 16A' (patented). Fruit quality is very similar between the three female cultivars, 'AU Golden Dragon', 'AU Golden Sunshine' and 'Hort 16A' (patented), however they differ in bloom date, fruit maturity date, and fruit shape. 'AU Golden Tiger' blooms earlier than 'Matua' (not patented).

The specific differences between the 'AU Golden Tiger' cultivar and the 'Matua' (not patented) cultivar used as the male comparison cultivar is illustrated in Table 1.

TABLE 1

Comparison of 'AU Golden Tiger' and 'Matua' cultivars.

| | 'AU Golden Tiger' | 'Matua' |
|---|---|---|
| Plant | | |
| Plant: sex expression | male (flowers imperfect) | |
| Plant: ploidy | hexaploid | |
| Plant: vigor | strong | [medium] |
| Young shoot: hairs | present | |
| Young shoot: density of hairs | heavy | |

TABLE 1-continued

Comparison of 'AU Golden Tiger' and 'Matua' cultivars.

| | 'AU Golden Tiger' | 'Matua' |
|---|---|---|
| Young shoot: type of hairs | tomentose | |
| Young shoot: anthocyanin | absent | |
| coloration of growing tip | N199B | |
| Young shoot: anthocyanin | absent | |
| coloration of leaf axil | N199B | |
| Plant: average height and spread | plant is a vigorous vine. They are grown on a trellis (either a T-bar or pergola trellis system) in which the plant is allotted a certain space of which it rapidly fills and is maintained in this space by both winter and summer pruning. In the case of the T-bar trellis, the trellis space is eight feet long by six feet wide. The trellis is six feet off the ground and the plant is allowed each summer to grow and hang down on each side. | |
| Stem | | |
| Stem: coloration of leaf axil | weak; N199B | |
| Stem: diameter | | |
| Stem base diameter | 13.3 (12-15 mm) | 15.5 (13.75-17.74 mm) |
| Stem mid section diameter | 10.7 (9-12 mm) | 8.43 (7.55-9.74 mm) |
| Stem: dormant bud diameter | 5.5 (5.2-5.6 mm) | 7.12 (6.32-8.21 mm) |
| Stem: color on upper side of shoot | light brown to tan; N199B | |
| Stem: character of bark | somewhat rough | [smooth] |
| Stem: hairs | present | |
| Stem: conspicuousness of lenticels | conspicuous | |
| Stem: number of lenticels | 16 (140-180)/sq cm | 232 (174-303/sq cm) |
| Stem: color of lenticels | tan; N199C | |
| Stem: size of bud support | small-medium | |
| Stem: visibility of bud (dormant canes) | almost buried | |
| Stem: number of hairs visible on bud (dormant canes) | medium | |
| Stem: leaf scar | length 5.5 mm (3.9-6.4 mm) width 5.3 mm (4.7-6.1 mm) | |
| Leaf (Mature) | | |
| Leaf shape: | orbicular to broadly cordate | orbicular to obovate; occasionally reniforme (kidney-shaped, wider than long) |
| Leaf base shape: | cordate, lobes strongly overlapping | narrowly cordate, lobes touching to slightly overlapping |
| Leaf tip shape: | obtuse, rotund with broadly deltoid tip | broadly obtuse to somewhat refuse with broad cuspidate at tip |

TABLE 1-continued

Comparison of 'AU Golden Tiger' and 'Matua' cultivars.

| | 'AU Golden Tiger' | 'Matua' |
|---|---|---|
| Leaf margin: | entire to weakly and irregularly crenate | entire |
| Leaf adaxial surface: | medium green (147A); glabrous except for sparse, unbranched hairs along veins | |
| Leaf abaxial surface: | light green (147A); dense, stellate pubescence everywhere except along main veins which are densely tomentose with unbranched hairs | |
| Leaf length (cm): | 20.1 (17.2-22.8) | 16,8 (13.6-20.5) |
| Leaf width (cm): | 17.6 (14.2-20.6) | 14.1 (12.0-20.8) |
| Leaf ratio (l/w): | 1.1 (1.0-1.3) | 1.2 (0.9-1.4) |
| Leaf petiole length (cm): | 5.5 (4.4-7.4) | 4.2 (3.3-6.3) |
| Leaf 1° vein organization: | pinnate; veins terminating as small extended points or mucros at leaf margins | |
| Leaf 2° vein organization: | parallel | |
| Leaf puckering: | strong | moderate |
| Leaf variegation: | none | |
| Leaf spines on lower leaf surface: | none; dense stellate hairs | |
| Petiole: | 147C | |
| Pedicel: | n/a | |
| Flower | | |
| Inflorescence#: predominate number of flower buds/stem | mean 3.0 (range 1-5) | mean 2.4 (range 1-4) |
| 1° Pedicel length (cm): | 2.5 (1.8-3.5) | 2.6 (1.4-3.3) |

TABLE 1-continued

Comparison of 'AU Golden Tiger' and 'Matua' cultivars.

| | 'AU Golden Tiger' | 'Matua' |
|---|---|---|
| 2° Pedicel length (cm): | n/a | 0.9 (0.6-1.5) |
| Pedicel pubescence: | minutely, densely tomentose, unbranched | |
| Sepal#: | 5.6 (3.0-7.0) | 5.3 (4-7) |
| Sepal color: | greyed-green to slightly rust colored at margin, 191B | [rusty greenish] |
| Sepal pubescence: | minutely, densely tomentose, unbranched | |
| Flower color: | creamy white (158C) to orange (169A) | creamy white |
| Flower width (cm): | 5.2 (4.2-6.1) | 3.8 (3.6-4.1) |
| Petal orientation: | distinctly overlapping | overlapping, sides reflexed |
| Petal #: | 6.3 (5.0-7.0) | 6.0 (5-7) |
| Petal length (cm): | 2.4 (1.8-2.6) | 1.9 (1.6-2.1) |
| Petal width (cm): | 2.1 (1.6-2.6) | 1.5 (1.2-1.8) |
| Petal ratio (l/w): | 1.1 (1.0-1.3) | 1.3 (0.9-1.5) |
| Stamen#: | 167 (160-173) | |
| Anther length (mm): | 2.0-3.0 | |
| Filament: | 158C | |
| Anther: | 169D | |

Notes regarding Table 1:

1. Horticulture terminology is used in accordance with revised UPOV guidelines for kiwi.
2. Characters of comparison cultivar 'Matua' are noted opposite that character when significantly different.
3. 'Matua' plants were observed in the same replicated study as the new cultivar.
4. All dimensions are in millimeters unless otherwise stated; weights are in grams.
5. The RHS 1966 color chart was used to determine actual color.

What is claimed is:

1. A new and distinct variety of the species *Actinidia chinensis* Planch named 'AU Golden Tiger' substantially as described and illustrated herein.

* * * * *